US012721793B2

(12) United States Patent
Xing et al.

(10) Patent No.: US 12,721,793 B2
(45) Date of Patent: Sep. 1, 2026

(54) O/W EMULSION AND W/O EMULSION INVERTED THEREFROM, AND PERSONAL CARE COMPOSITION CONTAINING SAME

(71) Applicant: MOMENTIVE PERFORMANCE MATERIALS INC., Niskayuna, NY (US)

(72) Inventors: Zhimin Xing, Shanghai (CN); Yun Huang, Shanghai (CN); Jingya Dai, Shanghai (CN)

(73) Assignee: MOMENTIVE PERFORMANCE MATERIALS INC., Niskayuna, NY (US)

( * ) Notice: Subject to any disclaimer, the term of this patent is extended or adjusted under 35 U.S.C. 154(b) by 710 days.

(21) Appl. No.: 17/997,994

(22) PCT Filed: May 7, 2020

(86) PCT No.: PCT/CN2020/088932

§ 371 (c)(1),
(2) Date: Nov. 4, 2022

(87) PCT Pub. No.: WO2021/223143

PCT Pub. Date: Nov. 11, 2021

(65) Prior Publication Data

US 2023/0172817 A1 Jun. 8, 2023

(51) Int. Cl.

*A61K 8/06* (2006.01)
*A61K 8/894* (2006.01)
*A61K 8/895* (2006.01)
*A61Q 1/02* (2006.01)

(52) U.S. Cl.

CPC .............. *A61K 8/062* (2013.01); *A61K 8/894* (2013.01); *A61K 8/895* (2013.01); *A61Q 1/02* (2013.01); *A61K 2800/10* (2013.01); *A61K 2800/87* (2013.01)

(58) Field of Classification Search

CPC ........ A61K 8/062; A61K 8/894; A61K 8/895; A61K 2800/10; A61K 2800/87; A61K 2800/88; A61K 8/064; A61K 8/891; A61Q 1/02; A61Q 1/06; A61Q 1/10; A61Q 5/06; A61Q 19/00; C08G 77/12; C08G 77/20; C08G 77/46; C08L 83/04

See application file for complete search history.

(56) References Cited

U.S. PATENT DOCUMENTS 7,955,608 B2 6/2011 Sakuta et al.
10,512,602 B2* 12/2019 Xing ........................ A61Q 5/12
2009/0017081 A1* 1/2009 Takakura ............... A61K 8/064 424/59
2010/0291015 A1 11/2010 Barba et al.
2017/0348220 A1* 12/2017 Xing ........................ A61Q 1/02
2019/0060211 A1 2/2019 Limer et al.

FOREIGN PATENT DOCUMENTS

| | | | |
|---|---|---|---|
| CN | 107149559 | A | 9/2017 |
| EP | 1391193 | A1 | 2/2004 |
| JP | 2000063462 | A | 2/2000 |
| JP | 2005526865 | A | 9/2005 |
| JP | 4726598 | B2 | 7/2011 |
| JP | 2019518837 | A | 7/2019 |
| JP | 2020037664 | A | 3/2020 |
| KR | 19990088619 | A | 12/1999 |
| KR | 20190039471 | A | 4/2019 |
| WO | WO-02092048 | A2 | 11/2002 |
| WO | WO-2005016998 | A2 | 2/2005 |
| WO | WO-2006086264 | A1 | 8/2006 |
| WO | WO-2007097275 | A1 | 8/2007 |
| WO | WO-2007130412 | A2 | 11/2007 |
| WO | WO-2008045427 | A1 | 4/2008 |
| WO | WO-2009128883 | A1 | 10/2009 |
| WO | WO-2012006526 | A2 | 1/2012 |
| WO | WO-2013098934 | A1 | 7/2013 |
| WO | WO-2014066827 | A2 | 5/2014 |

OTHER PUBLICATIONS

Masucci et al. “Emulsion Stability Basics” 2017 (Year: 2017).*
Masucci “Emulsion Stability Basics” Endeavor Business Media. 2017. (Year: 2017).*
Database Gnpd Mintel, “Flawless Light Double-End Pen Concealer,” XP093366019, Id No. 6267039 (Jan. 15, 2019). -- see IDS filed May 13, 2026 (Year: 2019).*
International Search Report and Written Opinion for International Application PCT/CN2020/088932, mailed on Jan. 27, 2021, National Intellectual Property Administration, China, 13 pages.
Luo, Y., et al., Silicone Resin and its Application, pp. 227-228 (Chemical Industry Press, Beijing, China (2002)).
Unverified English language translation of Luo, Y., et al., Silicone Resin and its Application, pp. 227-228 (Chemical Industry Press, Beijing, China (2002)).
Database GNPD Mintel, “Flawless Light Double-End Pen Concealer,” XP093366019, ID No. 6267039 (Jan. 15, 2019).

* cited by examiner

*Primary Examiner* — Brian-Yong S Kwon
*Assistant Examiner* — Rajan Pragani

(57) ABSTRACT

It relates to an O/W emulsion which can be inverted to a W/O emulsion and the W/O emulsion inverted from the O/W emulsion, wherein the O/W emulsion is obtained from radical polymerization under emulsion polymerization reaction condition of at least one polyorganosiloxane having at least two aliphatic unsaturated carbon-carbon bonds, and optionally an organohydrogenpolysiloxane, in the presence of a polyether-modified polysiloxane. It also relates to preparation process of the O/W emulsion and the W/O emulsion, and a personal care composition containing the emulsion.

14 Claims, 2 Drawing Sheets

O/W EMULSION AND W/O EMULSION INVERTED THEREFROM, AND PERSONAL CARE COMPOSITION CONTAINING SAME

FIELD OF THE INVENTION

The present invention relates to an O/W (oil-in-water) emulsion which can be inverted to a W/O (water-in-oil) emulsion and the W/O emulsion inverted from the O/W emulsion. The present invention also relates to a preparation process of the O/W emulsion and the W/O emulsion, and a personal care composition containing the O/W emulsion or the W/O emulsion.

BACKGROUND OF THE INVENTION

Emulsions are widely applied in personal care products. The emulsions are generally defined as metastable colloids, and comprise two immiscible fluids, namely oil and water, with one being dispersed (dispersed phase) in the other (continuous phase) in presence of a surface-active agent. Depending on the types of the dispersed phase and the continuous phase, the emulsions can be divided into water-in-oil (W/O) and oil-in-water (O/W) emulsions. Conversion between these two types of emulsions is generally called phase inversion or emulsion inversion.

W/O emulsions can provide improved sensory benefits such as a silky feeling for personal care products, but there are few preparation methods which can provide W/O emulsions with long-term stability. Most of the W/O emulsions have been prepared by a mechanical emulsification method wherein the water phase is dispersed in the oil phase at a high shearing rate. However, the W/O emulsions thus prepared may not be stable, and the content of the water phase introduced by this method is relatively low. Thus, phase inversion method has attracted increasingly interest. A PIT (phase inversion temperature) method has been proposed wherein the temperature of the emulsion is elevated to above PIT temperature for initiating phase inversion. For the purpose of stability, however, the W/O emulsions prepared from the PIT method have to be stored at a temperature above the PIT temperature, and cannot be stored at room temperature. Adding an aqueous solution having a concentration of an electrolyte or an inorganic salt into the emulsions may decrease the PIT temperature, but the decrease in the amount of the PIT temperature depends on the concentration of the solution and is limited by the solubility of the inorganic salt. Besides, the application of the W/O emulsion containing high concentration of salt may be restricted. Therefore, it is desired to prepare a W/O emulsion from an O/W emulsion without heating or adding an inorganic salt.

Further, although the O/W emulsions have been more intensively studied than the W/O emulsions, very few of them can be inverted to W/O emulsions successfully.

SUMMARY OF THE INVENTION

In an aspect, the present invention relates to an O/W emulsion of a crosslinked silicone, wherein the O/W emulsion is obtained from radical polymerization under emulsion polymerization reaction condition of at least one polyorganosiloxane having at least two aliphatic unsaturated carbon-carbon bonds, and optionally an organohydrogenpolysiloxane, in the presence of a polyether-modified polysiloxane.

The O/W emulsion of the present invention can be prepared by a process comprising:

(a) combining the polyorganosiloxane with the polyether-modified polysiloxane and the optional organohydrogenpolysiloxane to obtain a mixture;

(b) adding an aqueous medium containing an emulsifying agent into the mixture under stirring; and (c) subjecting the mixture to a radical polymerization.

In another aspect, the present invention relates to a W/O emulsion obtained from phase inversion of the O/W emulsion of the present invention by adding an oil into said O/W emulsion.

In yet another aspect, the present invention relates to a personal care composition comprising the W/O emulsion or the O/W emulsion in accordance with the present invention.

Surprisingly, it has been found that the O/W emulsion of the present invention can be inverted to a W/O emulsion by increasing the volume fraction of the oil phase, for example, by simply mixing with common oil or grease, especially those used in personal care formulation to increase the volume fraction of the oil phase. After phase inversion, the internal cross-linked silicone formed by the emulsion polymerization enters and occupies the continuous phase through swelling in oil phase, and may act as a rheological additive in formulating a personal care product. The phase inversion ability of the O/W emulsion is of great benefit. The O/W will be compatible with water or aqueous components due to its aqueous continuous phase, and will also be compatible with oil or oily components due to phase inversion. Thus, the phase inversion emulsion of the present invention can facilitate introducing aqueous ingredients into W/O emulsions (including water/silicone oil emulsions) or oil-based formulations. The formulations, especially cosmetics formulations, formed from the emulsions of the present invention can provide excellent stability and excellent feeling-in-use with increased aqueous ingredients, giving good cushioning feel without any stickiness feel.

DESCRIPTION OF THE INVENTION

Figure 1:
FIG. 1 shows the photograph taken for the emulsion prepared in Example 1 before and after mixing with hemisqualane as an oil.
Figure 1:
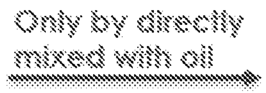
Figure 1:
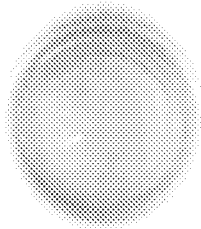

In the specification and claims herein, the following terms and expressions are to be understood as indicated.

The singular forms "a," "an," and "the" include the plural, and reference to a particular numerical value includes at least that particular value, unless the context clearly dictates otherwise.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of".

Other than in the working examples or where otherwise indicated, all numbers expressing amounts of materials, temperatures, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hydrocarbon group" means any hydrocarbon from which one or more hydrogen atoms has been removed and is inclusive of alkyl, alkenyl, alkynyl, cyclic alkyl, cyclic alkenyl, cyclic alkynyl, aryl, aralkyl and arenyl groups and is inclusive of hydrocarbon groups containing at least one heteroatom.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The term "heteroatom" means any of the Group 13-17 elements except carbon and includes, for example, oxygen, nitrogen, silicon, sulfur, phosphorus, fluorine, chlorine, bromine and iodine.

In one embodiment, hydrocarbon group(s), where present, contain up to 60 carbon atoms, in another embodiment up to 30 carbon atoms and in yet another embodiment up to 20 carbon atoms.

Useful hydrocarbon groups include alkyl groups examples of which are methyl, ethyl, n-propyl, isopropyl, n-butyl, isobutyl, tert-butyl, n-pentyl, isopentyl, neopentyl and tert-pentyl; hexyl such as n-hexyl; heptyl such as n-heptyl; octyl such as n-octyl, isooctyl and 2,2,4-trimethylpentyl; nonyl such as n-nonyl; decyl such as n-decyl; and cycloalkyl, such as cyclopentyl, cyclohexyl, cycloheptyl and methylcyclohexyl. Examples of alkenyl groups include vinyl, propenyl, allyl, methallyl, cyclohexenyl, norbornenyl, ethylnorbornenyl, ethylidenyl norbornane, ethylidene norbornyl, ethylidenylnorbornene and ethylidene norbornenyl. Examples of alkynyl groups include acetylenyl, propargyl and methylacetylenyl. Examples of aryl groups include phenyl, naphthyl; o-, m- and p-tolyl, xylyl, ethylphenyl and benzyl.

The terms and expressions "hydrosilyl", "hydride", "silicone hydride", "SiH", are understood in the organosiloxane art to be used interchangeably and to designate polyorganosiloxanes that contain one or more hydrogen atoms bonded directly to silicon.

The term "emulsion" as used herein shall also be understood to include "microemulsion".

The term "oil" as used herein shall also be understood to include, but not be limited to, polysiloxane liquid such as silicone oil.

Terms or words used in the description and claims should not be restrictively interpreted as ordinary or dictionary meanings, but should be interpreted as meanings and concepts conforming to the inventive concept on the basis of a principle that an inventor can properly define the concept of a term to explain his or her own invention in the best ways.

The inventors of the present invention have surprisingly discovered an O/W emulsion of a crosslinked silicone which can be inverted to a W/O emulsion by increasing the volume fraction of the oil phase, wherein the O/W emulsion is obtained from radical polymerization under emulsion polymerization reaction condition of at least one polyorganosiloxane having at least two aliphatic unsaturated carbon-carbon bonds, and optionally an organohydrogenpolysiloxane, in the presence of a polyether-modified polysiloxane.

The polyorganosiloxane has at least two aliphatic unsaturated carbon-carbon bonds which can subject to free radical addition polymerization reaction to form a crosslinked silicone in the internal phase of the O/W emulsion. The number of the aliphatic unsaturated carbon-carbon bonds may be, for example, 2 to about 1000, preferably 2 to about 500, more preferably 2 to about 100.

In a preferred embodiment, the polyorganosiloxane contains at least two alkenyl/alkynl groups. When organohydrogenpolysiloxane is present, the radical addition polymerization reaction involves not only the radical polymerization of the alkenyl/alkynl groups in the polyorganosiloxane, but also the hydrosilylation reaction between Si—H in the organohydrogenpolysiloxane and alkenyl/alkynl groups in the polysiloxane. The polyorganosiloxane may also contain Si—H functionality.

In an embodiment, the polyorganosiloxane having at least two aliphatic unsaturated carbon-carbon bonds is of the general formula (I):

$$M_g M^H_h M^V_i M^F_j D_k D^H_l D^V_m D^F_n T_o T^H_p T^V_q T^F_r Q_s \quad \text{formula (I)}$$

wherein $M=R^{21}R^{22}R^{23}SiO_{1/2}$;
$M^H=R^{24}R^{25}HSiO_{1/2}$;
$M^V=R^{26}R^{27}R^{28}SiO_{1/2}$;
$M^F=R^{29}R^{30}R^FSiO_{1/2}$;
$D=R^{31}R^{32}SiO_{2/2}$;
$D^H=R^{33}HSiO_{2/2}$;
$D^V=R^{34}R^{35}SiO_{2/2}$;
$D^F=R^{36}R^FSiO_{2/2}$;
$T=R^{37}SiO_{3/2}$;
$T^H=HSiO_{3/2}$;
$T^V=R^{38}SiO_{3/2}$;
$T^F=R^FSiO_{3/2}$; and
$Q=SiO_{4/2}$ in which $R^{21}$, $R^{22}$, $R^{23}$, $R^{24}$, $R^{25}$, $R^{27}$, $R^{28}$, $R^{31}$, $R^{32}$, $R^{33}$, $R^{35}$ and $R^{37}$ each independently is a monovalent hydrocarbon group of up to 60 carbon atoms, specifically of up to 30 carbon atoms and more specifically of up to 20 carbon atoms; $R^{26}$, $R^{34}$ and $R^{38}$ each independently is an ethylenically unsaturated group of up to 30 carbon atoms, specifically of up to 20 carbon atoms and more specifically of up to 10 carbon atoms; $R^{29}$, $R^{30}$ and $R^{36}$ each independently is a monovalent hydrocarbon group of up to 60 carbon atoms, more specifically of up to 30 carbon atoms and still more specifically of up to 20 carbon atoms, or $R^F$; each $R^F$ independently is a monovalent alkoxy group or ether group of up to 60 carbon atoms, more specifically of up to 30 carbon atoms and still more specifically of up to 20 carbon atoms; and, subscripts g, h, i, j, k, 1, m, n, o, p, q, r and s each independently is an integer of 0 to 1000 subject to the limitation that i+m+q≥2, for example an integer of 2 to about 500.

In a preferred embodiment, the polyorganosiloxane is at least one member selected from the group consisting of:

$$M^V_i D_k D^V_m M_{2-i} \quad \text{(I-1)}$$

wherein $M^V$, D, $D^V$ and M are as previously defined and subscripts i, k and m are integers subject to the limitation that i is 0 to 2; k is 0 to 1000, specifically 10 to 600 and more specifically 10 to 500; m is 0 to 100, more specifically 0 to 50; and $R^{26}$ and $R^{34}$ each independently is selected from the group consisting of vinyl, allyl, methallyl, acrylate or alkacrylate group, preferably vinyl or allyl;

$$M^V_i Q_s \quad \text{(I-2)}$$

wherein $M^V$ and Q are as previously defined and subscripts i and s are integers subject to the limitation that i≥1, specifically ≥2, and more specifically ≥3; s≥1, specifically ≥2, and more specifically ≥3; and i+s is 2 to 50, specifically 2 to 20, and more specifically 2 to 15; and each $R^{26}$ is selected from the group consisting of vinyl, allyl, methallyl, acrylate or alkacrylate group, preferably vinyl or allyl.

In an embodiment, the organohydrogenpolysiloxane is present and is of the general formula (I):

$$M_g M^H_h M^V_i M^F_j D_k D^H_l D^V_m D^F_n T_o T^H_p T^V_q T^F_r Q_s \quad \text{formula (I)}$$

wherein M, $M^H$, $M^V$, $M^F$, D, $D^H$, $D^V$, $D^F$, T, $T^H$, $T^V$, $T^F$ and Q are as previously defined, and subscripts g, h, i, j, k, l, m, n, o, p, q, r and s each independently is an integer of 0 to 500, specifically 0 to 200, and more specifically 0 to 100, subject to the limitations that (1) h+l+p≥1, specifically ≥2, and more specifically ≥8, and (2) when i+m+q≥2, the formulae (I) defined for the polyorganosiloxane and for the organohydrogenpolysiloxane are different.

In a preferred embodiment, the organohydrogenpolysiloxane is at least one member selected from the group consisting of:

$$M^H_h D_k D^H_l M_{2-h} \quad \text{(I-3)}$$

wherein $M^H$, D, $D^H$ and M are as previously defined and h, k and 1 are 0 or a positive number subject to the limitation that h is 0 to 2; k is 10 to 300, specifically 10 to 200, and more specifically 20 to 200; 1 is 0 to 50, specifically 0 to 20, and more specifically 1 to 10; and h+l is 1 to 100, more specifically 1 to 32 and still more specifically 2 to 12;

$$M^H_h Q_s \quad \text{(I-4)}$$

wherein $M^H$ and Q are as previously defined and subscripts h and s are integers subject to the limitation that h≥1, specifically ≥2, and more specifically ≥3; s≥1, specifically ≥2, and more specifically ≥3; and i+s is 2 to 50, specifically 2 to 20, and more specifically 2 to 15.

The ratio of total ethylenically unsaturated groups (including the ones present in polyorganosiloxane and organohydrogenpolysiloxane, if any) to total Si—H functionalities (including the ones present in polyorganosiloxane and organohydrogenpolysiloxane, if present) should be at least 1 and advantageously at least 2. On a weight basis, the weight ratio of total polyorganosiloxane to total organohydrogenpolysiloxane can vary widely, e.g., from 100:0 to 1:99, or from 100:0 to 50:50, or from 100:0 to 80:20.

The viscosities of polyorganosiloxane and organohydrogenpolysiloxane can vary widely. For example, polyorganosiloxane can have a viscosity as measured by Brookfield Rotary Viscometry of from 0.0002 to 1000 Pa·s, specifically 0.001 Pa·s to 100 Pa·s. The organohydrogenpolysiloxane can have a viscosity as measured by Brookfield Rotary Viscometry of from 0.001 to 50 Pa·s, specifically 0.002 to 10 Pa·s.

In most cases, polyorganosiloxane and organohydrogenpolysiloxane will be present within the O/W emulsion polymerization reaction mixture at the onset of polymerization. However, it is within the scope of the invention to commence polymerization of polyorganosiloxane alone and only thereafter but before completion of polymerization of polyorganosiloxane to introduce optional organohydrogenpolysiloxane into the emulsion reaction medium whereby unreacted $M^V$, $D^V$ and/or $T^V$ unit present in polyorganosiloxane will undergo hydrosilylation by $M^H$, $D^H$ and/or $T^H$ unit present in organohydrogenpolysiloxane. Delayed addition of organohydrogenpolysiloxane to polyorganosiloxane can be advantageous when preparing an interpenetrating polymer network (IPN) or a core-shell structure.

The "polyether-modified polysiloxane" used herein refers to a polysiloxane wherein one or more polyether moieties are bonded to the Si atom(s) in the backbone of the polysiloxane directly or via a divalent hydrocarbon group. The polyether moiety is composed of one or more alkylene oxide groups. The alkylene oxide group is preferably at least one selected from ethylene oxide group, propylene oxide group and butylene group. The Si atom to which the polyether moiety is bonded can be located in any of the M unit ($SiO_{1/2}$), D unit (SiO) or T unit ($SiO_{3/2}$) unit, preferably M unit and/or D unit, more preferably M unit. The divalent hydrocarbon group is preferably a divalent linear or branched alkylene group having 1 to about 20 carbon atoms, more preferably 2 to about 10 carbon atoms, and further more preferably 3 to 6 carbon atoms.

In addition to the polyether moiety, the polyether-modified polysiloxane may further contain other functionality, such as alkoxy group, aryloxy group, an amino group, an ester group, an amide or an epoxide group, which can be bonded to the Si atom in the backbone of the polysiloxane directly or via a divalent hydrocarbon group, for example the ones listed above with regard to polyether moiety.

In a preferred embodiment, the polyether-modified polysiloxane is of the general formula (II):

$$M_a^1 M_b^2 M_c^3 D_d^1 D_e^2 D_f^3 \quad \text{formula (II)}$$

wherein:

$M^1=R^1R^2R^3SiO_{1/2}$
$M^2=R^4R^5R^6SiO_{1/2}$
$M^3=R^7R^8R^9SiO_{1/2}$
$D^1=R^{10}R^{11}SiO_{2/2}$
$D^2=R^{12}R^{13}SiO_{2/2}$
$D^3=R^{14}R^{15}SiO_{2/2}$ where in Formula (II), $R^1$, $R^2$, $R^3$, $R^4$, $R^5$, $R^7$, $R^8$, $R^{10}$, $R^{11}$, $R^{12}$ and $R^{14}$ each independently is a monovalent hydrocarbon group having up to about 60 carbon atoms, preferably an alkyl or an aryl having up to 10 carbon atoms, more preferably an alkyl having 1-4 carbon carbons or a phenyl, and even more preferably a methyl;

$R^6$ and $R^{13}$ each independently is —$R^{16}$—O—$(C_2H_4O)_x(C_3H_6O)_y(C_4H_8O)_z$—$R^{17}$, where $R^{16}$ is a divalent linear or branched alkylene group optionally containing a oxygen atom or a nitrogen atom and having 1 to about 20 carbon atoms, preferably 2 to about 10 carbon atoms, more preferably about 3 to 6 carbon atoms; $R^{17}$ is selected from hydrogen, alkyl, acyl (—C(O)R, R being an alkyl group) or an ester group (—C(O)OR, R being an alkyl group) having 1 to about 20 carbon atoms, preferably 1 to about 6 carbon atoms; and subscripts x, y and z each independently is an integer of 0 to about 200, preferably 1 to about 100, and more preferably 2 to about 20, subject to the limitation that $1 \le x+y+z \le 200$;

$R^9$ and $R^{15}$ each independently is a linear or branched alkyl group of 4 to about 20 carbon atoms optionally containing F atom; a linear or branched alkoxy group or aryloxy group of up to about 20 carbon atoms; or a divalent alkylene group optionally containing F atom and having 1 to about 20 carbon atoms, preferably 3 to about 10 carbon atoms, terminated with an alkoxy group, aryloxy group, an amino group, an ester group, an amide or an epoxide group;

the subscripts a, b, c, d, e, f each independently is an integer of 0 to 200 subject to the limitation that $b+e \ge 1$.

In a further preferred embodiment, the polyether-modified polysiloxane is at least one member selected from the group consisting of:

$$M_2^1 D_d^1 D_e^2 \quad \text{(II-1)}$$

wherein $M^1$, $D^1$ and $D^2$ are as previously defined for formula (II), d is 1 to about 200, preferably 1 to about 100; and e is 1 to about 200, preferably 1 to about 100; and $$M_b^2 D_d^1 D_e^2 M_{2-b}^1 \quad \text{(II-2)}$$

wherein $M^1$, $M^2$, $D^1$ and $D^2$ are as previously defined previously defined for formula (II), b is 1 or 2, d is 1 to 200, preferably 1 to about 100; and e is 1 to 200, preferably 1 to about 100.

The polyether-modified silicone may be prepared by hydrosilylation of Si—H functionalized polysiloxane with a vinyl-containing polyether in the presence of Pt catalyst, which is well known in the art. The polyether-modified silicone are also commercially available, for example, PEG-3 dimethicone, PEG-6 dimethicone, PEG-7 dimethicone, PEG-8 dimethicone, PEG-9 dimethicone, PEG-10 dimethicone, PEG-12 dimethicone, PEG-14 dimethicone, PEG-17 dimethicone and PEG/PPG-20/15 dimethicone (all from Momentive Performance Materials).

Based on 100 parts by weight of the total amount of the polyorganosiloxane having at least two aliphatic unsaturated carbon-carbon bonds and the organohydrogenpolysiloxane (if present), the polyether-modified silicone is used in an amount of about 5 to about 50 parts by weight, preferably about 8 to about 35 parts by weight, and more preferably 10 to about 30 parts by weight.

Free radical-initiated polymerization of polyorganosiloxane and hydrosilylation of polyorganosiloxane with organohydrogenpolysiloxane (if present) can be carried out in an O/W emulsion polymerization reaction medium employing conventional or otherwise known emulsion polymerization procedures.

In such emulsion polymerization procedures, the dispersed oil phase of the emulsion reaction mixture includes polyorganosiloxane, polyether modified silicone, optional organohydrogenpolysiloxane and optional organic solvent and/or swelling agent (compatibilizer).

The continuous aqueous phase of the emulsion reaction medium includes water and water-soluble or water-miscible components such as emulsifier, free radical initiator and optional components such as stabilizers, co-stabilizers, chain transfer agents, and the like. In general, the oil phase can constitute from 1 to 80, and advantageously from 30 to 70 weight percent of the emulsion polymerization reaction medium with the aqueous phase making up the balance.

In an embodiment, the O/W emulsion is prepared by a process comprising:

(a) combining the polyorganosiloxane with the polyether-modified polysiloxane, the optional organohydrogen-polysiloxane and optional organic solvent and/or swelling agent (compatibilizer) to obtain a mixture;

(b) adding an aqueous medium containing an emulsifying agent, a free radical initiator and optional stabilizers and/or co-stabilizers into the mixture under stirring; and (c) subjecting the mixture to a radical polymerization.

Solvents and/or swelling agents (compatibilizers) can be incorporated in the oil phase of the emulsion polymerization reaction medium. Suitable solvents/swelling agents include non-reactive polyorganosiloxanes having a viscosity from 0.002 Pa·s to 0.2 Pa·s, for example, methicones, alkyl methicone such as octyl methicone, dimethicone, alkyl dimethicone, phenyl dimethicone, amino dimethicone, trimethylsiloxysilicate and polymethylsilsesquioxane; hydrocarbons such as isodecane, hexadecane and squalane; triglycerides such as caprylic triglyceride; esters such as cetyl palmitate and isopropyl myristate; and ethers such as dipropylene glycol butyl ether. Such solvents/swelling agents can represent up to 95 weight percent of the oil phase of the O/W emulsion reaction medium.

Suitable emulsifiers include those of the nonionic and anionic types and their mixtures. Suitable nonionic emulsifiers include any of those heretofore employed in emulsion polymerization processes such as the alcohol ethoxylates, polyoxyethylene lauryl ethers, polyoxyethylene monostearates, and the like. Similarly, useful anionic emulsifiers include those known to be useful in emulsion polymerization procedures such as the alkali metal sulfonates, sulfates, phosphates and sulfosuccinate surfactants. Specific examples of these surfactants include alkali metal sulforesorcinates; sulfonated glyceryl esters of fatty acids; salts of sulfonated monovalent alcohol esters; sulfonated aromatic hydrocarbon alkali salts such as sodium alpha-naphthalene monosulfonate; sulfates such as sodium lauryl sulfate, sodium cetostearyl sulfate, triethanol amine lauryl sulfate and sodium lauryl ether sulfate; phosphates such as the potassium salts of cetyl phosphate; and, sulfosuccinates such as disodium lauryl sulfosuccinates. In a preferred embodiment, nonionic emulsifiers such as polyoxyethylene lauryl ethers, polyoxyethylene monostearates or combination thereof are used.

The free radical initiator can be selected from, for example, azo initiators, inorganic peroxides, organic peroxides and redox initiators. Azo initiators include (2,2'-azobis (2-methylpropionamidine) dihydrochloride. Inorganic peroxides include ammonium persulfate, sodium persulfate and potassium persulfate. Organic peroxides include benzoyl peroxide and dilauroyl peroxide. Redox initiators include ammonium persulfates and 2-hydroxy-2-sulfinatoacetic acid disodium salt, hydrogen peroxide and absorbic acid and potassium persulfate and tetramethylethylenediamine. The free radical reaction can also be initiated by high energy sources such as ultrasound and radiation in accordance with conventional and otherwise known procedures.

Suitable stabilizers include polymeric steric stabilizers such as partially hydrolyzed poly(vinyl acetate), thickeners such as guar gum, cellulose and its derivatives, polyacrylates and polyacrylic acid copolymers. Suitable co-stabilizers include polyethers such as ethylene oxide/propylene oxide copolymers, glyols, glycerin and electrolytes such as potassium chloride and calcium chloride.

Particle size of the crosslinked silicone in the O/W emulsion herein may be effectively controlled by selection and/or adjustment of the viscosity of the polyorganosiloxane prior to emulsification as well as adjustment of the temperature, mixing speed and/or emulsifier used in preparing the emulsion. In one embodiment, the particle size of silicone gel emulsion can be from 10 nm to 100 microns, and specifically from 100 nm to 30 microns as determined by dynamic laser scattering analyzer such as laser particle size analyzer LS230.

The combination step (a) and step (b) may be carried out at room temperature or at an elevated temperature of not higher than, for example 100° C., preferably not higher than 80° C.

Depending on the nature of the selected free radical initiator, the radical polymerization step (c) can be carried out at a temperatures of from 40° C. to 100° C., preferably 50° C. to 90° C. for a period of about 1 to 10 hours, preferably 2 to 5 hours to provide the O/W emulsion of crosslinked silicone according to the present invention.

The O/W emulsion of the present invention can phase invert to W/O emulsion after mixing with compatible oil. Without being bounded to theory, when the compatible oil is added externally into the O/W emulsion, the internal crosslinked silicone formed from radical polymerization can "bloom" into the oil phase with the aid of the polyether modified polysiloxane which may facilitate contact of the internal crosslinked silicone with the external oil. Then, the crosslinked silicone having good compatibility with general organic oil (including silicone oil) swells in external phase with external oil, and water phase becomes an internal phase dispersed in the oil phase. Both emulsification and viscosity can be enhanced from the same ingredients. This phase inversion emulsion of crosslinked silicone gives good cushioning feel without any stickiness feel after phase inversion for the application formulation.

In addition to visual observation, decreased conductivity can be an indicative of successful phase inversion from an O/W emulsion to a W/O emulsion. When such phase inversion occurs, the conductivity will be greatly decreased to about lower than 5 μs/cm and in some embodiments even lower than 1 μs/cm. Any method known for measuring conductivity may be used herein. For example, the conductivity may be measured using SevenExcellence multiparameter (Mettler Toledo).

The crosslinked silicone O/W emulsion herein and also the W/O emulsion inverted from this O/W emulsion can advantageously be incorporated in any of numerous types of personal care compositions. Such personal care compositions include but are not limited to applications such as deodorants, antiperspirants, antiperspirant/deodorants, stick and roll-on preparations, skin lotions, moisturizers, toners, cleansing preparations, styling gels, hair dyes, hair color preparations, hair straighteners, nail polish, nail polish remover, sunscreens, anti-aging preparations, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus preparations, night and day skin care preparations, tanning preparations, hand liquids, non-woven preparations for personal care, facial tissue, baby lotions, facial cleansing preparations, hair cuticle coats, gels, foam baths, body washes, scrubbing cleansers, controlled-release personal care preparations, hair shampoos, hair conditioners, hair sprays, skin care moisturizing mists, skin wipes, pore skin wipes, pore cleaners, blemish reducers, skin exfoliators, skin desquamation enhancers, anti-acne preparations, skin towelettes, skin cloths, depilatory preparations, personal care lubricants, nail coloring preparations and drug delivery systems for topically applied therapeutics and medicinals.

It is desirable that in all embodiments of the O/W gel emulsion herein the emulsion reaction medium be devoid of precious metal hydrosilylation reaction catalyst, e.g., of the platinum-containing type, where the resulting crosslinked polyorganosiloxane O/W gel emulsion or crosslinked polyorganosiloxane isolated therefrom is intended to be incorporated in a personal care product in view of the propensity of such catalysts to cause discoloration or decreased clarity.

EXAMPLES

The present invention will be more specifically explained with reference to Examples, but these Examples shall not be construed as to limit the scope of the present invention. In the descriptions below, moreover, "part(s)" denotes "part(s) by weight" unless otherwise stated. The viscosity is measured by LVDV-II+ viscometer (Brookfield).

Example 1

A mixture was formed by mixing: 40 parts by weight of vinyl group-containing dimethylpolysiloxane ($M^VD_{560}D^V{}_{36}M^V$) having a viscosity of about 5 Pa·s at 25° C., 5 parts by weight of bis-hydrogen dimethicone ($M^HD_{20}M^H$) having a viscosity of about 0.02 Pa·s at 25° C., 20 parts by weight of hemisqualane (APRINNOVA), 10 parts by weight of PEG 9 dimethicone (Momentive Performance Materials), and 2 parts by weight of steareth 21 (Croda). Then, the mixture was charged with 10 parts by weight of initial water and 0.2 parts by weight of sodium surfactin (Kaneka Corporation) with vigorous stirring to get a stable emulsion. Deionized water was further added to give a non-volatile content of 50 percent by weight. The emulsion was then heated to 60° C. and adjusted to pH 4, followed by the addition of 0.05 parts by weight ammonium persulfate to commence free radical polymerization of the vinyl group-containing dimethylpolysiloxane and its hydrosilylation with the bis-hydrogen dimethicone. After 4 hours, no SiH was found in the resulting stable O/W emulsion as determined by the fermentation tube method described in Luo et al., "Silicone Resin and its Application", Chemical Industry Press, Beijing, pp. 227-228 (2002). The emulsion was adjusted to pH 7 with triethanolamine and 0.8 parts by weight of phenoxyethanol was added thereto as a preservative. The O/W emulsion thus prepared was stable and had a viscosity of 4600 cps as measured by LVDV-II+ viscometer (Brookfield) using S64 rotator at 60 rpm.

Then, the prepared O/W emulsion was mixed with hemisqualane as an oil in a weight ratio of 3:7 at room temperature. The state of the emulsion before and after mixing with the oil is shown in FIG. 1. The emulsion after mixing with hemisqualane was measured for conductivity by SevenExcellence multiparameter (Mettler Toledo) at room temperature and for viscosity by LVDV-II+ viscometer (Brookfield) using S4 rotator at 60 rpm. The conductivity is 0.2 μs/cm, and the viscosity is 6,500 cPs. The results show that the prepared O/W emulsion has inverted to a W/O after mixing with the oil.

Example 2

A mixture was formed by mixing at 50° C.: 50 parts by weight of vinyl group-containing dimethylpolysiloxane ($M^VD_{200}M^V$) having a viscosity of about 2 Pa·s at 25° C., 10 parts by weight of a silicone resin with hydrogen group ($M^H{}_8Q_4$), 5 parts by weight of cetearyl methicone (Momentive Performance Materials), 3 parts by weight of PEG 8 dimethicone (Momentive Performance Materials), 8 parts by weight of PEG 9 dimethicone (Momentive Performance Materials), 2 parts by weight of C30-45 alkyl dimethicone (Momentive Performance Materials) and 80 parts by weight of dimethicone having a viscosity of about 0.01 Pa·s at 25° C. (Momentive Performance Materials). Then, the mixture was charged with an admixture of 1.5 parts by weight of sodium cetostearyl sulfate, 6 parts by weight of polyoxyethylene lauryl ether, 8 parts by weight of polyoxyethylene monostearate and 20 parts by weight of deionized water with vigorous stirring to provide a stable emulsion. Deionized water was further added to give a non-volatile content of 50 percent by weight. The emulsion was adjusted to a temperature of 40° C. and a pH of 4, followed by the addition thereto of 0.1 parts by weight each of hydrogen peroxide and ascorbic acid to commence free radical polymerization of the vinyl group-containing dimethylpolysiloxane and its hydrosilylation with the hydrogen group in $M^H{}_8Q_4$. After 4 hours, no SiH was found in the emulsion as determined by the fermentation tube method. Following adjustment of the pH to 5.5 with citric acid, the emulsion was added with 0.5 parts by weight of sodium benzoate as a preservative. The O/W emulsion thus prepared was stable and had a viscosity of 4800 cps as measured by LVDV-II+ viscometer (Brookfield) using S64 rotator at 60 rpm.

Example 3

A mixture was formed by mixing at 80° C.: 100 parts by weight of silicone resin with vinyl group ($M^V{}_8Q_4$) having a viscosity of about 0.5 Pa·s at 25° C., 15 parts by weight of PEG 9 dimethicone (Momentive Performance Materials), 2 parts by weight of PEG/PPG-20/15 dimethicone (Momentive Performance Materials), 10 parts by weight of methylhydrogenpolysiloxane ($M^HD_{200}M^H$) having a viscosity of about 0.2 Pa·s at 25° C., 40 parts by weight of isopropyl myristate and 0.5 part of lauroyl peroxide. Then, the mixture was charged with an admixture of 4 parts by weight of steareth 2/21 (Croda), 4 parts by weight of polyoxyethylene monostearate and 20 parts by weight of deionized water with vigorous stirring to provide a stable emulsion. Deionized water was further added to give a non-volatile content of 50 percent by weight. Then, the emulsion was adjusted to a temperature of 80° C. to commence free radical polymerization and free radical hydrosilylation. After 4 hours, unreacted SiH in the emulsion was found to be less than 0.1 cc/g when measured by the fermentation tube method. Following adjustment of the pH to 6.5 with triethanolamine, 0.8 parts by weight of phenoxyethanol was added to the emulsion as a preservative. The O/W emulsion thus prepared was stable and had a viscosity of 3200 cps as measured by LVDV-II+ viscometer (Brookfield) using S64 rotator at 60 rpm.

Example 4

A mixture was formed by mixing 40 parts by weight of vinyl group-containing dimethylpolysiloxane ($M^VD_{560}D^V{}_{36}M^V$) having a viscosity of about 5 Pa·s at 25° C., 20 parts by weight of hemisqualane (APRINNOVA), 10 parts by weight of PEG 9 dimethicone (Momentive Performance Materials), and 2 parts by weight of steareth 21 (Croda). Then, the mixture was charged with 10 parts by weight of initial water and 0.2 parts by weight of sodium surfactin (Kaneka Corporation) with vigorous stirring to provide a stable emulsion. Deionized water was further added to give a non-volatile content of 50 percent by weight. Then, the emulsion was adjusted to a temperature of 80° C. to commence free radical polymerization which was completed in 4 hours. Then, the emulsion was added with 0.8 parts by weight of phenoxyethanol as a preservative and 0.2 parts by weight of guar gum as a thickener. The O/W emulsion thus prepared was stable and had a viscosity of 4000 cps as measured by LVDV-II+ viscometer (Brookfield) using S64 rotator at 60 rpm.

Figure 2A:
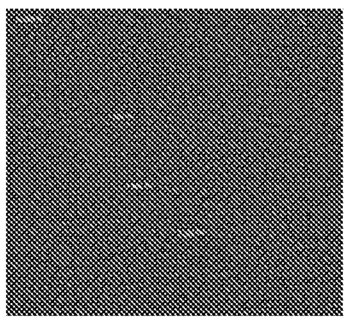
FIGS. 2*a* and 2*b* show the micrographs of the emulsion prepared in Example 4 before phase inversion (2*a*) and after phase inversion (2*b*) using Silsoft 034 as an oil.
Figure 2B:
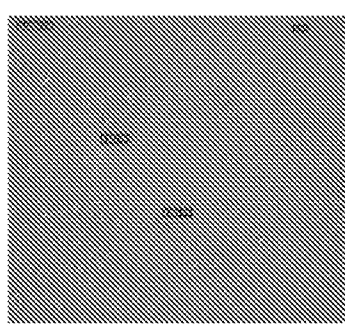

Then, the prepared O/W emulsion was mixed with Silsoft 034 (Momentive Performance Materials) as an oil in a ratio of 1:1.2 at room temperature. The micrographs of the emulsion before and after mixing with the oil are shown in FIGS. 2*a* and 2*b*, respectively. The emulsion before and after mixing with the oil was measured for conductivity by SevenExcellence multiparameter (Mettler Toledo) at room temperature and for viscosity by LVDV-II+ viscometer (Brookfield) using S64 (before) or S4 (after) rotator at 60 rpm. The conductivity is decreased from 36.8 μs/cm to 1.6 μs/cm, and the viscosity is increased from 4,000 cPs to 112,000 cPs. The results show that the prepared O/W emulsion has inverted to a W/O after mixing with the oil.

The D4 (octamethycyclotetrasiloxane), D5 (decamethycyclopentasiloxane) and D6 (dodecamethylcyclohexasiloxane) contents of the O/W emulsions of Examples 1-4 were measured by conventional gas chromatography (GC). The results of the measurements are set forth below in Table 1. In general, it is advantageous to provide an O/W emulsion in which the total content of D4, D5 and D6 is controlled to less than 1,000 ppm, especially for personal care products.

TABLE 1 properties of emulsion

| No. | D4% | D5% | D6% |
|---|---|---|---|
| Example 1 | 0.02 | 0.03 | 0.03 |
| Example 2 | 0.02 | 0.03 | 0.03 |
| Example 3 | 0.02 | 0.03 | 0.03 |
| Example 4 | 0.02 | 0.02 | 0.02 |

Comparative Example 1

A mixture was formed by mixing: 40 parts by weight of vinyl group-containing dimethylpolysiloxane ($M^VD_{560}D^V{}_{36}M^V$) having a viscosity of about 5 Pa·s at 25° C., 20 parts by weight of hemisqualane (APRINNOVA), 10 parts by weight of PEG 9 dimethicone (Momentive Performance Materials), 2 parts by weight of steareth 21 (Croda). Then, the mixture was charged with 10 parts by weight of initial water and 0.2 parts by weight of sodium surfactin (Kaneka Corporation) with vigorous stirring to provide a stable emulsion. Followed by adding 0.1 parts by weight of 0.33 wt % $H_2PtCl_6$ in ethanol, deionized water was further added to give a non-volatile content of 50 percent by weight. Then, the emulsion was adjusted to a temperature of 80° C. to commence polymerization. After 4 hours, the emulsion was added with 0.8 parts by weight of phenoxyethanol as a preservative and 0.2 parts by weight of guar gum as a thickener. The O/W emulsion thus prepared had a viscosity of 4200 cps as measured by LVDV-II+ viscometer (Brookfield) using S64 rotator at 60 rpm.

Figure 3A:
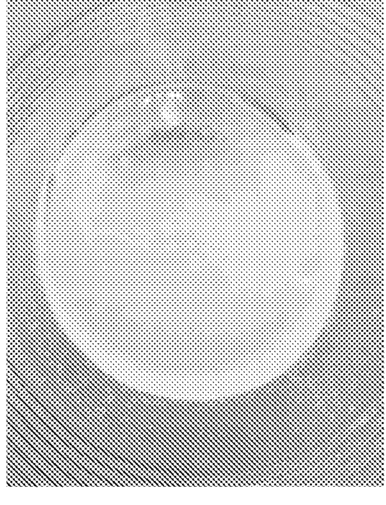
FIGS. 3*a* and 3*b* show the photographs taken for the emulsions prepared in Example 4 (3*a*) and in Comparative Example 1 (4*b*) demulsified with isopropyl alcohol (IPA).
Figure 3B:
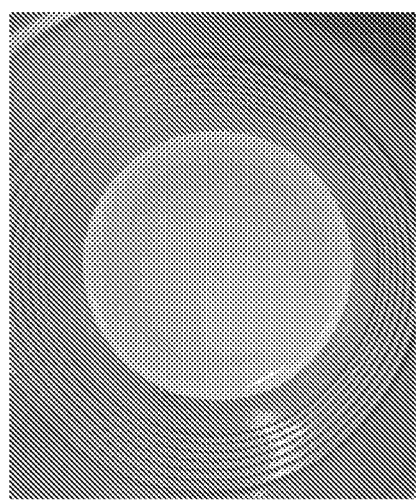

The emulsions from Example 4 and Comparative Example 1 were demulsified respectively with isopropyl alcohol (IPA). The photographs showing the demulsified result were illustrated in FIG. 3*a* (Example 4) and 3b (Comparative Example 1) respectively. The demulsified O/W emulsion of Example 4 showed small size gels while no such gels were present in the demulsified emulsion of Comparative Example 1, which means that the internal phase in Comparative Example 1 was little crosslinked (if any).

Comparative Example 2

A mixture was formed by mixing at 80° C.: 100 parts by weight of a silicone resin with vinyl group ($M^VD_{560}D^V{}_{36}M^V$) having a viscosity of about 0.5 Pa·s at 25° C., 10 parts by weight of methylhydrogenpolysiloxane ($M^HD_{200}M^H$) having a viscosity of about 0.2 Pa·s at 25° C. and 40 parts by weight of isopropyl myristate and 0.5 part by weight of lauroyl peroxide. Then, the mixture was charged with an admixture of 4 parts by weight of steareth 2/21 (Croda), 4 parts by weight of polyoxyethylene monostearate and 20 parts by weight of deionized water with vigorous stirring to provide a stable emulsion. Deionized water was further added to give a non-volatile content of 50 percent by weight. Then, the emulsion was adjusted to a temperature of 80° C. to commence free radical polymerization and free radical hydrosilylation. After 4 hours, unreacted SiH in the emulsion was found to be 0.1 cc/g when measured by the fermentation tube method. Following adjustment of the pH to 7, 0.8 parts by weight of phenoxyethanol was added to the emulsion as a preservative. The O/W emulsion thus prepared had a viscosity of 4500 cps as measured by LVDV-II+ viscometer (Brookfield) using S64 rotator at 60 rpm.

Test a (Phase Inversion Test)

Figure 4:
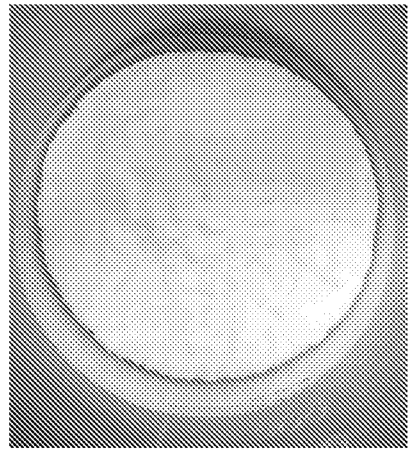
FIG. 4 shows the photographs taken for the emulsion prepared in Comparative Example 2 after mixing with hemisqualane as an oil in a ratio of 1:1.
Figure 4:
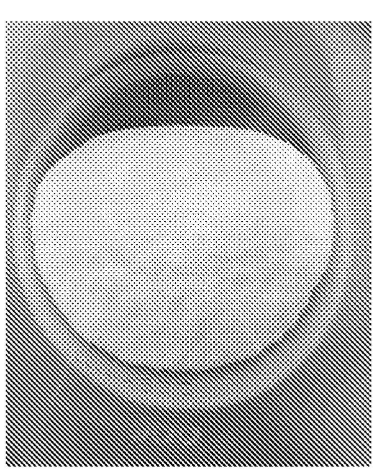

The emulsion prepared in Comparative Example 2 was mixed with hemisqualane as an oil in a ratio of 1:1. However, the emulsion could not invert phase after mixing with the oil. As shown in FIG. 4, the white emulsion was on the bottom, and the hemisqualane oil was on the surface.

Test B (Water Compatibility Test)

Figure 5A:
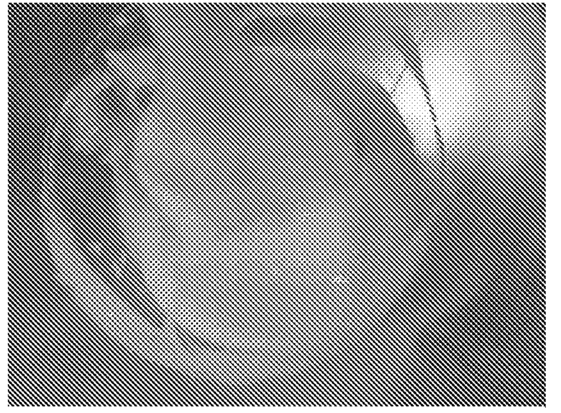
FIGS. 5*a* and 5*b* show the photographs taken for the emulsion prepared in Comparative Example 2 after mixing with PEG-10 dimethicone (5*a*), and further with deionized water (5*b*).
Figure 5B:
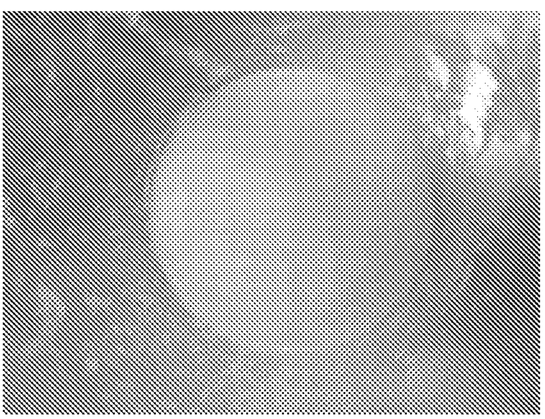

The emulsion prepared in Comparative Example 2 in an amount of 30 g was mixed with 5 g PEG-10 dimethicone, and the resultant changed to a thick paste. Then, 50 g deionized water was added into the resultant under stirring, and the thick paste became thin with many little chips on the surface indicative of a bad water dilution, as shown in FIG. 5.

The results of Comparative Example 2 in comparison with Examples 1-4 show the function of the polyether silicone for phase inversion. If the polyether silicone is not used during the emulsion polymerization, the prepared O/W emulsion cannot be inverted to a W/O emulsion by mixing with an oil. If the polyether silicone is introduced after the emulsion polymerization, the emulsion will turn to a thick paste, and has poor compatibility with water.

Examples 5-10 illustrate various personal care compositions formulated with a phase inversion emulsion initiated from O/W emulsion of the present invention. Examples 5-9 illustrate oil-based formulations, and Example 10 illustrate a water-based formulation.

Example 5 Avocado Cream

| | Component | Supplier | Wt % |
|---|---|---|---|
| Part A | | | |
| 1 | Example 1 | | 27.40 |
| 2 | *Aloe barbadensis* extract | XI'AN SoBeo PharmTech Co., Ltd | 0.5 |
| 3 | Hydrolyzed wheat protein | Shandong Gaoguang SoBeo PharmTech Co.,Ltd | 0.1 |
| 4 | Glycerin | Collinslab | 2.00 |
| Part B | | | |
| 5 | Avocado oil | Guangzhou hanbaisi | 40.00 |
| 6 | Silsoft 034 fluid | Momentive | 20.00 |
| 7 | Element PDMS 5 | Momentive | 10.00 |
| 8 | phenoxyethanol | | 0.5 |

Procedure:

1. Blending Part A components.
2. Pre-mixing Part B components.
3. Slowly charging part B directly into part A with stirring.
4. High speed stirring for 3-5 mins.

Example 6: HD Foundation

| | Component | | Wt % |
|---|---|---|---|
| PartA | | | |
| 1 | Example 1 | | 27.40 |
| 2 | *Aloe barbadensis* extract | XI'AN SoBeo PharmTech Co., Ltd | 0.30 |
| 3 | Hydrolyzed wheat protein | XI'AN SoBeo PharmTech Co., Ltd | 0.20 |
| 4 | Glycerin | Collinslab | 1.00 |
| Part B | | | |
| 5 | olive oil | Guangzhou hanbaisi | 10.00 |
| 6 | Silsoft 034 fluid | Momentive | 10.00 |
| 7 | Element PDMS 5 | Momentive | 14.80 |
| Part C | | | |
| 8 | Silsoft 034 fluid | Momentive | 8.00 |
| 9 | ALT-TSR-10 (Titanium Dioxide, Aluminum Hydroxide, Triethoxycaprylylsilane) | MIYOSHI | 8.00 |
| 10 | ALT-MSY-10 (Iron oxides, Triethoxycaprylylsilane) | MIYOSHI | 0.08 |
| 11 | ALT-MSR-10 (Iron oxides, Triethoxycaprylylsilane) | MIYOSHI | 0.20 |
| 12 | ALT-MSB-10 (Iron oxides, Triethoxycaprylylsilane) | MIYOSHI | 0.02 |
| 13 | phenoxyethanol | | 0.5 |

Procedure:

1. Blending Part A components.
2. Pre-mixing Part B components.
3. Pre-mixing Part C components.
4. Slowly charging part B directly into part A with stirring, and then high-speed stirring the mixture for 3~5 mins.
5. Blending the AB mixture and pre-mixed Part C.

Example 7: Concealer Balm

| | Component | | Wt % |
|---|---|---|---|
| Part A | | | |
| 1 | Arlacel A-165 | Croda | 4.00 |
| 2 | SF1642 wax | Momentive | 4.00 |
| 3 | 2039N (Candelilla Wax) | Kahl | 3.00 |
| 4 | 4511N(Ozokerite) | Kahl | 8.00 |
| 5 | Tospearl 3000A microsphere | Momentive | 5.00 |
| 6 | Velvesil Magic-B gel | Momentive | 20.00 |
| 7 | ALT-TSR-10 | MIYOSHI | 10.00 |
| 8 | Softouch CC 6097 | Momentive | 3.00 |
| 9 | UNIPURE Yellow LC 181ASEM | Sensient Cosmetic & Fragrances | 0.50 |
| 10 | UNIPURE Red LC 380ASEM | Sensient Cosmetic & Fragrances | 0.30 |
| 11 | UNIPURE Black LC 989ASEM | Sensient Cosmetic & Fragrances | 0.16 |
| 12 | Crodamol IPM | Croda | 12.00 |
| 13 | Crodamol GTCC | Croda | 5.00 |
| 14 | Vaseline | Xibao | 5.00 |
| 15 | Silsoft 034 fluid | Momentive | 10.00 |
| 16 | phenoxyethanol | | 0.5 |

-continued

| | Component | | Wt % |
|---|---|---|---|
| Part B | | | |
| 17 | Example 4 | Momentive | 5.04 |
| 18 | SS4230 fluid | Momentive | 5.00 |

Procedure:

1. Mixing all the components of Part A and heating to 80° C.
2. Pre-mixing Part B components.
3. After cooling down to 65° C., adding Part A into Part B under stirring.

Example 8: Lip Balm

| | Component | | Wt % |
|---|---|---|---|
| Part A | | | |
| 1 | SF1642 wax | Momentive | 6 |
| 2 | 8019(Beewax) | Kahl | 9 |
| 3 | 2442(Carnauba Wax) | Kahl | 5 |
| 4 | 1847(Microcrystal Wax) | Kahl | 5 |
| 5 | 2039N(Candelilla Wax) | Kahl | 5 |
| 6 | ESTOL-1543(Ethylhexyl Palmitate) | Croda | 9 |
| 7 | ESTOL-3603(Caprylic/ Capric Triglyceride) | Croda | 8 |
| 8 | squalane | Zhuhai jiayi | 6 |
| 9 | Velvesil Magic-B gel | Momentive | 10 |
| 10 | Silsoft 034 fluid | Momentive | 5 |
| Part B | | | |
| 11 | Lippovol MACMacadamia Ternifolia Seed Oil) | Lippovol | 24 |
| 12 | Example 4 | | 8 |
| 13 | phenoxyethanol | | 0.5 |

Procedure:

1. Mixing all the components of Part A and heating to 80° C.
2. Pre-mixing Part B components.
3. After cooling down to 65° C., adding Part A into Part B under stirring.

Example 9: Silky Cream

| | Component | | Wt % |
|---|---|---|---|
| Part A | | | |
| 1 | TEGO Alkanol 1618 (Cetearyl Alcohol) | Evonik | 1.5 |
| 2 | Silsoft 034 fluid | Momentive | 3 |
| 3 | TEGOSOFT CT(Caprylic/ Capric Triglycerides) | Evonik | 5 |
| 4 | SIMMONDSIA CHINENSIS (JOJOBA) SEED OIL | Ecooil | 2 |
| Part B | | | |
| 5 | Glycerin | Collinslab | 5 |
| 6 | Keltrol CG-T(Xanthan Gum) | CP Keko | 0.1 |
| 7 | TEGO Care SE 121 (Sucrose Stearate) | Evonik | 3 |
| 8 | Carbopol Ultrez 30 polymer | Lubrizol | 0.25 |
| 9 | Demineralized Water | | 74.3 |

-continued

| | Component | | Wt % |
|---|---|---|---|
| Part C | | | |
| 10 | Triethanol amine | Collinslab | 0.25 |
| Part D | | | |
| 11 | Example 2 | | 5 |
| 12 | phenoxyethanol | | 0.5 |

Procedure:

1. Mixing all the components of Part A, and heating Part A to about 80° C.
2. Dissolving Part B components in water, and heating Part B to about 80° C.
3. Adding Part A into Part B with stirring, and homogenizing for several minutes.
4. Adding Part C into Part A/B with stirring.
5. Adding Part D into Part A/B/C with stirring.

Example 10: Double Layer Hair Spray

| | Component | | Wt % |
|---|---|---|---|
| Part A | | | |
| 1 | water | | 67.00 |
| 2 | glycerin | Collinslab | 2.00 |
| 3 | Propylene glycol | Collinslab | 1.00 |
| 4 | phenoxyethanol | | 0.5 |
| 5 | fragrance | | 0.1 |
| Part B | | | |
| 7 | Example 1 | | 10.00 |
| Part C | | | |
| 8 | Element 14 PDMS 5A | Momentive | 20.00 |

Procedure:

1. charging Part C into Part B with stirring.
2. Mixing Part A components.
3. Adding Part A into Part B/C mixture.

Each of the formulations obtained from Examples 5-10 was tested for stability at 50° C. oven for 1 week. The formulations remained unchanged.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A process of preparing an O/W emulsion of a cross-linked silicone, comprising:

combining at least one polyorganosiloxane having at least two aliphatic unsaturated carbon-carbon bonds, and optionally an organohydrogenpolysiloxane, in the presence of a polyether-modified polysiloxane to form a mixture, wherein the polyether-modified polysiloxane is used in an amount of about 5 to about 50 parts by weight based on 100 parts by weight of the total amount of the polyorganosiloxane having at least two aliphatic unsaturated carbon-carbon bonds and the organohydrogenpolysiloxane when present; and subjecting the mixture to radical polymerization under emulsion polymerization reaction conditions.

2. The process of claim 1, wherein the at least one polyorganosiloxane is of the general formula (I):

$$M_g M^H_h M^V_i M^F_j D_k D^H_l D^V_m D^F_n T_o T^H_p T^V_q T^F_r Q_s \quad \text{formula (I)}$$

wherein $M=R^{21}R^{22}R^{23}SiO_{1/2}$;
$M^H=R^{24}R^{25}HSiO_{1/2}$;
$M^V=R^{26}R^{27}R^{28}SiO_{1/2}$;
$M^F=R^{29}R^{30}R^FSiO_{1/2}$;
$D=R^{31}R^{32}SiO_{2/2}$;
$D^H=R^{33}HSiO_{2/2}$;
$D^V=R^{34}R^{35}SiO_{2/2}$;
$D^F=R^{36}R^FSiO_{2/2}$;
$T=R^{37}SiO_{3/2}$;
$T^H=HSiO_{3/2}$;
$T^V=R^{38}SiO_{3/2}$;
$T^F=R^FSiO_{3/2}$; and
$Q=SiO_{4/2}$ in which $R^{21}$, $R^{22}$, $R^{23}$, $R^{24}$, $R^{25}$, $R^{27}$, $R^{28}$, $R^{31}$, $R^{32}$, $R^{33}$, $R^{35}$ and $R^{37}$ each independently is a monovalent hydrocarbon group of up to 60 carbon atoms; $R^{26}$, $R^{34}$ and $R^{38}$ each independently is an ethylenically unsaturated group of up to 30 carbon atoms; $R^{29}$, $R^{30}$ and $R^{36}$ each independently is a monovalent hydrocarbon group of up to 60 carbon atoms or $R^F$; each $R^F$ independently is a monovalent alkoxy group or ether group of up to 60 carbon atoms; and, subscripts g, h, i, j, k, l, m, n, o, p, q, r and s each independently is an integer of 0 to 1000 subject to the limitation that $i+m+q\geq 2$.

3. The process of claim 1, wherein the polyorganosiloxane is at least one member selected from the group consisting of:

$$M^V_i D_k D^V_m M_{2-i} \quad \text{(I-1)}$$

wherein $M^V$, D, $D^V$ and M are as previously defined and subscripts i, k and m are integers subject to the limitation that i is 0 to 2, k is 0 to 600, m is 0 to 100, and $R^{26}$ and $R^{34}$ each independently is selected from the group consisting of vinyl, allyl, methallyl, acrylate or alkacrylate group;

$$M^V_i Q_s \quad \text{(I-2)}$$

wherein $M^V$ and Q are as previously defined and subscripts i and s are integers subject to the limitation that $i\geq 1$, $s\geq 1$ and i+s is 2 to 50, and each $R^{26}$ is selected from the group consisting of vinyl, allyl, methallyl, acrylate or alkacrylate group.

4. The process of claim 1, wherein the combining further comprises the organohydrogenpolysiloxane, wherein the organohydrogenpolysiloxane is of the general formula (I):

$$M_g M^H_h M^V_i M^F_j D_k D^H_l D^V_m D^F_n T_o T^H_p T^V_q T^F_r Q_s \quad \text{formula (I)}$$

wherein

M, $M^H$, $M^V$, $M^F$, D, $D^H$, $D^V$, $D^F$, T, $T^H$, $T^V$, $T^F$ and Q are as previously defined, and subscripts g, h, i, j, k, l, m, n, o, p, q, r and s each independently is an integer of 0 to 500 subject to the limitations that $h+l+p\geq 1$, and when $i+m+q\geq 2$, the formulae (I) defined for the polyorganosiloxane and for the organohydrogenpolysiloxane are different.

5. The process of claim 1, wherein the combining further comprises the organohydrogenpolysiloxane, wherein the organohydrogenpolysiloxane is at least one member selected from the group consisting of:

$$M^H_h D_k D^H_l M_{2-h} \quad \text{(I-3)}$$

wherein $M^H$, D, $D^H$ and M are as previously defined and h, k and l are 0 or a positive number subject to the limitation that k is 10 to 300, l is 0 to 50, h is 0 to 2 and h+l is 1 to 100;

$$M^H_h Q_s \quad \text{(I-4)}$$

wherein $M^H$ and Q are as previously defined and subscripts h and s are integers subject to the limitation that $h\geq 1$, $s\geq 1$ and i+s is 2 to 50.

6. The process of claim 1, wherein the polyether-modified polysiloxane is of the general formula (II):

$$M^1_a M^2_b M^3_c D^1_d D^2_e D^3_f \quad \text{formula (II)}$$

wherein:

$M^1=R^1R^2R^3SiO_{1/2}$
$M^2=R^4R^5R^6SiO_{1/2}$
$M^3=R^7R^8R^9SiO_{1/2}$
$D^1=R^{10}R^{11}SiO_{2/2}$
$D^2=R^{12}R^{13}SiO_{2/2}$
$D^3=R^{14}R^{15}SiO_{2/2}$ where in Formula (II), $R^1$, $R^2$, $R^3$, $R^4$, $R^5$, $R^7$, $R^8$, $R^{10}$, $R^{11}$, $R^{12}$ and $R^{14}$ each independently is an alkyl having up to about 60 carbon atoms or an aryl group;

$R^6$ and $R^{13}$ each independently is $-R^{16}-O-(C_2H_4O)_x(C_3H_6O)_y(C_4H_8O)_z-R^{17}$, where $R^{16}$ is a divalent alkylene group having 1 to about 20 carbon atoms, $R^{17}$ is selected from hydrogen, alkyl, acyl or an ester group having 1 to about 20 carbon atoms, and subscripts x, y and z each independently is an integer of 0 to 200 subject to the limitation that $1\leq x+y+z\leq 200$;

$R^9$ and $R^{15}$ each independently is a linear or branched alkyl group of 4 to about 20 carbon atoms; a monovalent alkoxy group or aryloxy group of up to about 20 carbon atoms; or a divalent alkylene group having 1 to about 20 carbon atoms terminated with an alkoxy group, aryloxy group, an amino group, an ester group, an amide or an epoxide group;

the subscripts a, b, c, d, e, f each independently is an integer of 0 to 200 subject to the limitation that b+e≥1.

7. The process of claim 1, wherein the polyether-modified polysiloxane is at least one member selected from the group consisting of:

$$M^1_2 D^1_d D^2_e \qquad \text{(II-1)}$$

wherein $M^1$, $D^1$ and $D^2$ are as previously defined, dis 1 to 200, and e is 1 to 200; and $$M^2_b D^1_d D^2_e M^1_{2-b} \qquad \text{(II-2)}$$

wherein $M^1$, $M^2$, $D^1$ and $D^2$ are as previously defined, b is 1 or 2, d is 1 to 200, and e is 1 to 200.

8. The process of claim 1, further comprising:

adding under stirring an aqueous medium containing an emulsifying agent into the mixture formed by combining the polyorganosiloxane with the polyether-modified polysiloxane and the optional organohydrogensiloxane.

9. A process of preparing a W/O emulsion comprising:

subjecting the O/W emulsion prepared by the process of claim 1 to phase inversion by adding an oil to the O/W emulsion.

10. A personal care composition comprising the O/W emulsion prepared by the process of claim 1.

11. A personal care application comprising the personal care composition of claim 10, wherein the personal care application is selected from the group consisting of deodorants, antiperspirants, antiperspirant/deodorants, stick and roll-on preparations, skin lotions, moisturizers, toners, cleansing preparations, styling gels, hair dyes, hair color preparations, hair straighteners, nail polish, nail polish remover, sunscreens, anti-aging preparations, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus preparations, night and day skin care preparations, tanning preparations, hand liquids, non-woven preparations for personal care, facial tissue, baby lotions, facial cleansing preparations, hair cuticle coats, gels, foam baths, body washes, scrubbing cleansers, controlled-release personal care preparations, hair shampoos, hair conditioners, hair sprays, skin care moisturizing mists, skin wipes, pore skin wipes, pore cleaners, blemish reducers, skin exfoliators, skin desquamation enhancers, anti-acne preparations, skin towelettes, skin cloths, depilatory preparations, personal care lubricants, nail coloring preparations, and drug delivery systems for topically applied therapeutics and medicinals.

12. A personal care composition comprising the W/O emulsion prepared by the process of claim 9.

13. A personal care application comprising the personal care composition of claim 12, wherein the personal care application is selected from the group consisting of deodorants, antiperspirants, antiperspirant/deodorants, stick and roll-on preparations, skin lotions, moisturizers, toners, cleansing preparations, styling gels, hair dyes, hair color preparations, hair straighteners, nail polish, nail polish remover, sunscreens, anti-aging preparations, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus preparations, night and day skin care preparations, tanning preparations, hand liquids, non-woven preparations for personal care, facial tissue, baby lotions, facial cleansing preparations, hair cuticle coats, gels, foam baths, body washes, scrubbing cleansers, controlled-release personal care preparations, hair shampoos, hair conditioners, hair sprays, skin care moisturizing mists, skin wipes, pore skin wipes, pore cleaners, blemish reducers, skin exfoliators, skin desquamation enhancers, anti-acne preparations, skin towelettes, skin cloths, depilatory preparations, personal care lubricants, nail coloring preparations, and drug delivery systems for topically applied therapeutics and medicinals.

14. The O/W emulsion prepared by the process of claim 1, wherein the combining further comprises the organohydrogenpolysiloxane.

* * * * *